United States Patent [19]

Galasko et al.

[11] Patent Number: 4,953,393
[45] Date of Patent: Sep. 4, 1990

[54] TRANSDUCER

[75] Inventors: Philip E. Galasko, Sandton; Frans J. Kruger, Pretoria, both of South Africa

[73] Assignee: Philip Elliot Galasko, Sandton, South Africa

[21] Appl. No.: 69,309

[22] Filed: Jul. 2, 1987

[30] Foreign Application Priority Data

Jul. 4, 1986 [ZA] South Africa ............... 86/4988
Dec. 23, 1986 [ZA] South Africa ............... 86/9672

[51] Int. Cl.$^5$ ................... B60C 23/02; G01L 9/12
[52] U.S. Cl. ........................... 73/146.5; 73/336.5; 336/30; 361/283
[58] Field of Search ............... 73/146.2, 146.3, 146.5, 73/146.8, 301, 336.5, 337, 778, 775, DIG. 1, 862.59, 862.68, 774, 779, 780; 361/283; 336/30; 340/365 A, 365 L, 365 C

[56] References Cited

U.S. PATENT DOCUMENTS

| | | | |
|---|---|---|---|
| 2,982,127 | 5/1961 | Scott | 73/775 |
| 4,233,523 | 11/1980 | Jarder | 336/20 |
| 4,335,608 | 6/1982 | Wood | 73/301 |
| 4,389,884 | 6/1983 | Agulia | 73/146.5 |
| 4,409,586 | 10/1983 | Hochstein | 73/146.5 |
| 4,578,992 | 4/1986 | Galasko | 73/146.5 |

FOREIGN PATENT DOCUMENTS

| | | |
|---|---|---|
| 0108176 | 5/1984 | European Pat. Off. . |
| 0202375 | 5/1985 | European Pat. Off. . |
| 3205705 | 8/1983 | Fed. Rep. of Germany . |

Primary Examiner—Donald O. Woodiel
Attorney, Agent, or Firm—Ladas & Parry

[57] ABSTRACT

A passive electrically operable monitoring means has an inherent resistance and a characteristic capacitance and inductance only, so that the monitoring means has a predetermined natural frequency of oscillation. Variations in a physical parameter being monitored by the monitoring means will cause the characteristic capacitance and/or inductance to vary thereby varying the natural frequency of oscillation of the monitoring means. A transducer includes an excitation means for exciting the monitoring means and a sensing means for sensing the natural frequency of oscillation of the monitoring means. The excitation means includes a pulse generating means for exciting the monitoring means with a string of pulses having a repetition rate suitably lower than the natural frequency of oscillation of the monitoring means so that damped oscillations occur in the monitoring means.

26 Claims, 3 Drawing Sheets

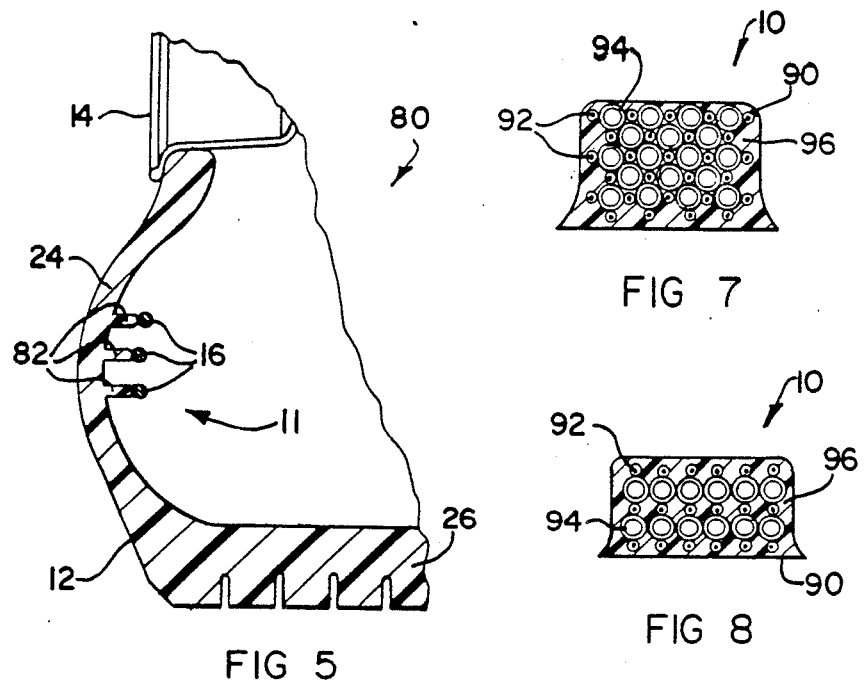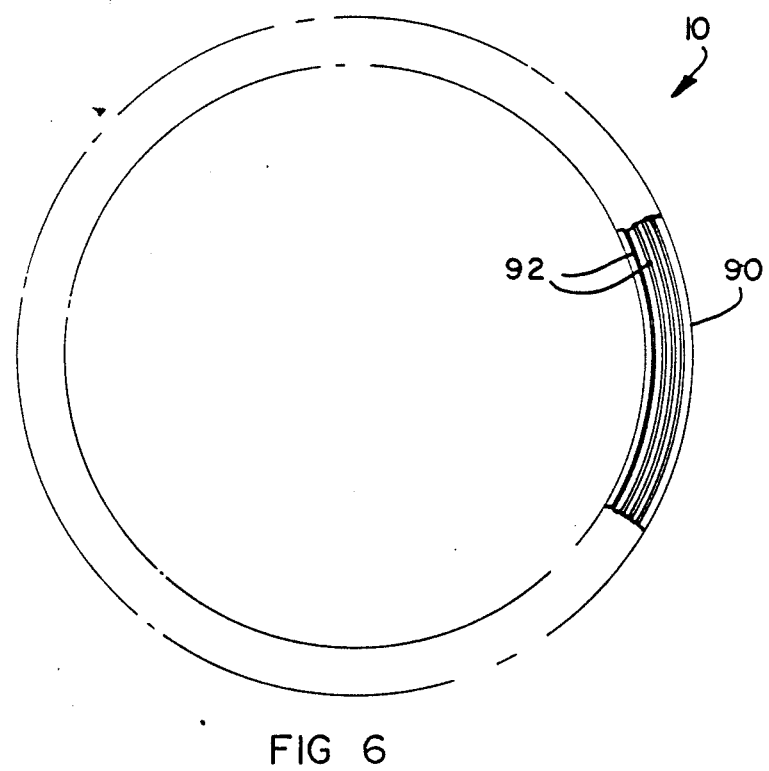

TRANSDUCER

This invention relates to a transducer. More particularly it relates to a passive electrically operable monitoring means for use with a transducer for providing an electrical signal representative of a physical parameter, and to such a transducer. The invention also relates to a method of monitoring a physical parameter. The particular parameters that may be monitored are pressure or force, temperature and humidity. Further in this regard, a particular transducer to which the invention relates is for monitoring the pressure of a tire and correspondingly to a method of monitoring the pressure in a tire. The invention then extends to a tire and a wheel which carries the transducer and also to a vehicle which has such a tire and wheel.

According to one aspect of the invention, there is provided a passive electrically operable monitoring means for use with a transducer for monitoring a physical parameter, the monitoring means having an inherent resistance and a characteristic capacitance and inductance a selected one of the characteristic capacitance and inductance being variable such that the monitoring means has a natural frequency of oscillation that varies in accordance with variations in the parameter being monitored.

It will be appreciated that as the monitoring means has only a characteristic inductance and capacitance, it does not have a discrete capacitance or inductance.

In one embodiment of the invention, the monitoring means may comprise a length of conducting wire wound into a coil with spaces being provided between adjacent turns of the coil.

Then, when the parameter to be monitored is pressure or force, the turns may be resiliently arranged relative to one another. Preferably the monitoring means may include a resiliently flexible web arranged between the turns of the coil, with the turns being secured to the web so that, in use, as the web flexes under the effect of the pressure or force being monitored, the spacing between the turns varies thereby varying the characteristic inductance or capacitance of the coil, and hence its natural frequency of oscillation. It will be understood that in this form the coils may be arranged next to one another.

When the parameter to be monitored is temperature or humidity, the monitoring means may include a conduit defining means which defines a conduit for introducing a gas into proximity with the coil, so that as the temperature or humidity of the gas varies, the characteristic inductance or capacitance varies, thereby varying the natural frequency of oscillation of the coil.

The conduit defining means may include a length of tube which is coiled with the length of wire of the coil so that the tube is arranged between the turns of the coil.

Those skilled in the art will appreciate that the monitoring means could be defined in any number of ways. Hence, in another embodiment of the invention, the monitoring means may comprise at least two lengths of spaced conductors arranged in a two-wire transmission line or co-axial cable manner.

The spacing between the conductors or the effective length thereof may be variable to vary the natural frequency of oscillation of the monitoring means when the parameter to be monitored is pressure or force.

When the parameter to be monitored is temperature or humidity of the gas, the monitoring means may include a conduit defining means for defining a conduit whereby a gas can be introduced into spaces in proximity to the conductors.

Similarly, more than two lengths of conductors may be arranged adjacent to and spaced from one another in a resilient manner or with a conduit for the gas between the adjacent conductors. The ends of some or all of the conductors may be joined so that conductors forms an endless coil or they may not be joined so that each conductor is a D.C. open circuit. They may even, possibly, be joined by discrete impedance components or the ends of adjacent conductors may be connected by such discrete impedance components.

With reference to the pressure or force application, the conductors may be arranged to be resiliently spaced, in any suitable manner. Thus they may be secured to a resiliently flexible material which flexes as the pressure or force being monitored varies, so that the spacing of the conductors varies. Instead, the spacing between the conductors may be kept constant, and the effective length of the conductors may be varied. Hence, the ends of the conductors may be terminated in spring loaded short circuited terminations which, in use, are responsive to variations in the pressure or force being applied for varying the effective length of the conductors.

As indicated above, with a pressure transducer, one way of varying the characteristic inductance and/or capacitance of the circuit may be by varying the spacing of the conductors, or the length of the line. However, the same result could be obtained in other ways, for example, by maintaining the spacing of the conductors and the effective length of the line constant, and by varying an electro-magnetic value, such as the permittivity or permeability, of a medium between the turns of the coil or the conductors. Thus, the monitoring means may include a dielectric medium located between the turns of the coil or the length of conductors, as the case may be, the permittivity of the dielectric medium being variable in response to variations in the pressure or force applied thereto, for varying the natural frequency of oscillation of the monitoring means.

According to another aspect of the invention, there is provided a transducer for monitoring a physical parameter, the transducer including
a monitoring means as described above.,
an energising means for energising the monitoring means; and
a sensing means for sensing the natural frequency of oscillation of the monitoring means.

The energising means may include an energising coil which may be coupled electrically and/or magnetically to the monitoring means in a wireless manner for energising the monitoring means to cause the monitoring means to oscillate at its natural frequency of oscillation, it being appreciated that the energising coil is not mechanically coupled to the monitoring means.

The energising coil (or some other energy transmitting device that transmits energy in a wireless manner) may be located, or locatable, sufficiently close to the monitoring means to energise it and to cause oscillations therein at its natural frequency of oscillation. Preferably, the monitoring means minimally influences the energising means and vice versa. Thus, the energising coil may be loosely coupled to the monitoring means.

The transducer may include a pulse generating means for generating a string of pulses at a repetition rate sufficiently lower than the natural frequency of oscillation of the monitoring means so that damped oscillations occur in the monitoring means, in use.

The sensing means may include a sensing coil which is electrically and/or magnetically coupled to the monitoring means in a wireless manner. The sensing means is preferably also not mechanically connected to the monitoring means. The monitoring means is also, preferably, not influenced by the sensing means and vice versa, and hence the sensing coil may be loosely coupled to the monitoring means.

The invention extends still further to a tire which includes
  a casing; and
  a monitoring means as described above mounted within and rotatably fast with the casing.

If the monitoring means comprises a coil, the invention will accordingly extend to a tire having the coil fast therewith. The monitoring means will have at least a part thereof, and preferably all, in communication with the tire which, in use, gets pressurised. Thus, the monitoring means may be secured to an inside surface of the tire, conveniently of a side wall portion.

It will also be understood that the monitoring means could just as well be secured to a tube for the tire, or to a rim with which the tire is to be engaged.

As an extension of this aspect, the tire may be engaged with a rim to constitute a wheel, and as a further extension, the invention also encompasses a wheeled vehicle which includes a pressure transducer in accordance with the invention.

The energising means and the sensing means of the transducer may be mountable adjacent an exterior surface of a side wall of the casing.

It will be appreciated that a transducer as described above has a simple yet elegant construction, which is also extremely robust and reliable. The transducer is also extremely rugged and balanced so that it does not perturb a tire or anything else with which it is used.

According to yet a further aspect of the invention, there is provided a method of monitoring a physical parameter which includes
  energising a passive electrical monitoring means having a characteristic capacitance and characteristic inductance and an inherent resistance so that the monitoring means oscillates at a natural frequency of oscillation;
  causing the characteristic capacitance or the characteristic inductance to vary in accordance with variations in the parameter being monitored thereby to vary the natural frequency of oscillation of the monitoring means in response to variations in the parameter; and
  sensing the variations in the natural frequency of oscillation of the monitoring means to provide an indication of the variation in the parameter being monitored.

As described above, the monitoring means may comprise a length of conducting wire wound into a coil to provide a plurality of spaced turns, and when the parameter to be monitored is pressure or force, the method may then include varying the spacing between the coils to vary the characteristic capacitance or inductance of the coil, and hence its natural frequency of oscillation, in response to variations in the pressure or force being applied to the coil.

When the parameter to be monitored is humidity or temperature of a gas, the method may include introducing the gas into proximity to the turns of the coils so that the characteristic inductance or capacitance of the coil, and hence its natural frequency of oscillation, varies in response to variations in the humidity or the temperature of the gas.

The method may include introducing the gas in proximity to the turns of the coil by means of a conduit defining means, the conduit defining means being wound together with the length of conducting wire so that the conduit defining means is arranged between the turns of the coil.

Further, as previously described, when the monitoring means comprises at least two length of conductors which are arranged in a transmission line or co-axial cable manner, and when the parameter being monitored is pressure or force, the method may include varying the spacing between the conductors.

The method may include varying the effective length of the conductors by means of spring loaded tapered short circuited terminations which are responsive to the pressure or forces being applied.

The method may include introducing a gas into a space in proximity to the conductors when the parameter being monitored is the temperature or humidity of the gas.

When the monitoring means comprises a length of conducting wire wound into a coil to provide a plurality of spaced turns, the method may include, when the parameter being monitored is pressure or force, causing the permittivity or permeability of a medium between the turns to vary, thereby to vary the natural frequency of oscillation of the coil.

The method may then include locating a suitable material between the turns, the material being allowed to expand or to be compressed as the force or pressure being monitored, and which is exerted on the material, varies so that the permittivity of the material varies.

Instead, the method may include introducing a suitable material between the elements in proportion to the force or pressure being monitored, so that the permittivity of the medium between the turns varies.

The method may include energising the monitoring means with a string of pulses which has a repetition rate suitably lower than the natural frequency of oscillation of the monitoring means so that damped oscillations occur in the monitoring means.

The invention is now described, by way of examples, with reference to the accompanying drawings, in which:

FIGS. 2, 3, 4 and 5 show similar views of further embodiments in accordance with the invention;

FIG. 6 shows a partly section side view of a pressure transducer in accordance with a further aspect of the invention;

FIG. 7, 8 and 9 show sectional views of various embodiments of the transducer of FIG. 6.

Figure 1:
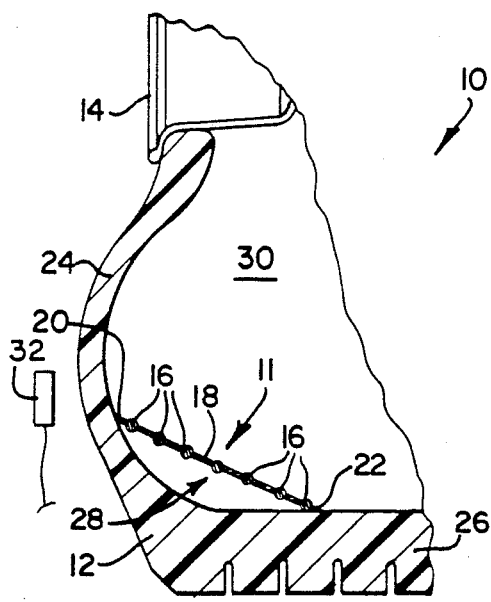
FIG. 1 shows a sectioned view of part of a wheel of a vehicle illustrating one embodiment of the invention.

Referring to FIG. 1, a first embodiment of a transducer in accordance with the invention is designated generally by reference numeral 10. The transducer 10 is associated with a pneumatic tire 12 which is mounted on a rim 14 to form a wheel for a vehicle (not shown).

The transducer 10 comprises a passive monitoring means which is essentially formed from a length of copper wire which is coiled to form a coil 11 having a plurality of turns 16. The diameter of the turns increases in a direction away from a side wall 24 of the tire 12 so that the coil is substantially frusto-conical. The turns 16 are secured to a flexible membrane 18 which is of a suitable resiliently flexible rubber or plastics material. The smaller end 20 of the membrane 18 is secured to the inner surface of the side wall 24 of the tire 12 and the other, larger end 22 is secured to the inner surface of a tread portion 26 of the tire 12, so that the membrane stretches between the side wall portion 24 and the tread portion 26 inside the tire. The membrane 18 accordingly defines a chamber 28 together with that portion of the inside surface of the tire 12 which it spans. The ends of the first turn and the last turn are open-circuited. It will be appreciated that the ends of the first turn and the last turn could also be terminated with a discrete impedance component.

It will be appreciated that the coil 11 formed by the turns 16 will have a characteristic inductance and capacitance only and it will oscillate at a particular natural frequency. It will further be appreciated that the characteristic inductance and capacitance will vary in accordance with the spacing of the turns. Thus, if the membrane 18 flexes, thereby varying the spacing of the turns 16, the natural frequency of oscillation will vary. Thus, as the pressure within a general chamber 30 defined by the tire 12 and the rim 14 varies in relation to the pressure in the chamber 28, so the membrane 18 will flex and the resulting natural frequency of oscillation will be representative of the pressure within the wheel.

The coil 11 formed by the turns 16 may be excited by means of an excitation coil 32 positioned adjacent the wheel in register with the turns 16. Similarly, once the coil 11 has been excited, the frequency of oscillation may be sensed by a similar coil 34 (see FIG. 12) which is also positioned adjacent the wheel, but in a diametrically opposed position to the coil 32. Thus, referring to FIG. 12, the coil 32 is supplied with pulses from an amplifier 36 that is connected in turn to a pulse generator 38. The amplifier 36 supplies the excitation coil 32 with pulses at a repetition rate that is substantially lower than the natural frequency of oscillation of the coil 11 in the tire, so that damped oscillations occur in the coil 11. Further, the excitation coil 32 and the coil 11 are loosely electrically and magnetically coupled so that the coil 11 is sufficiently excited without perturbing the signal in the coil 32 to any significant extent.

Figure 12:
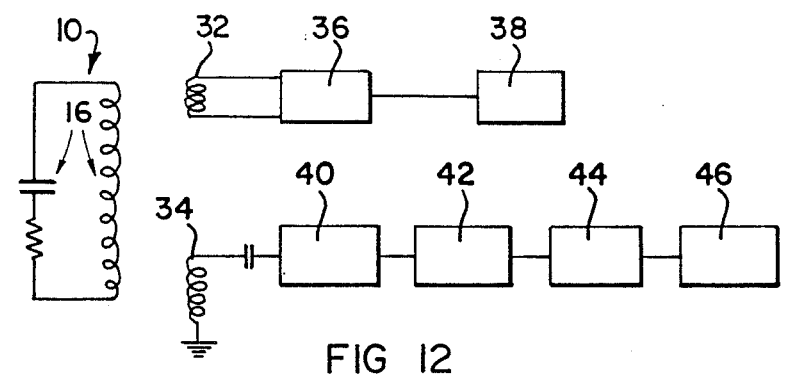
FIG. 12 shows in block diagram form circuitry for exciting any one of the transducers 7 FIGS. 1 to 11, which are shown by an equivalent circuit in FIG. 12, and sensing the resulting oscillations in the transducers.

Similarly, the sensing coil 34 is connected to a series circuit comprising an amplifier 40, a signal-conditioning circuit 42, a frequency-to-D.C. voltage convertor 44 and a comparator 46. Thus, the coil 34 senses the oscillations in the coil 11 and provides a signal representative thereof. The coil 34 and the coil 11 are also loosely magnetically and electrically coupled so that the sensing coil 34 does not affect the natural frequency of oscillation of the coil 11. The signal provided by the sensing coil 34 is amplified by the amplifier 40, conditioned by the circuit 42, and is converted to a D.C. voltage signal which is then compared by the comparator 46 with a predetermined value and if the signal provided by the convertor 44 varies relative to the predetermined value to indicate that the pressure in the tire has dropped below a predetermined value, then the comparator 46 provides an alarm signal. It will be appreciated that the components of the circuitry illustrated in FIG. 12 are standard items which can be readily realised by a person skilled in the art. Accordingly, these components need not be described any further.

Figure 2:
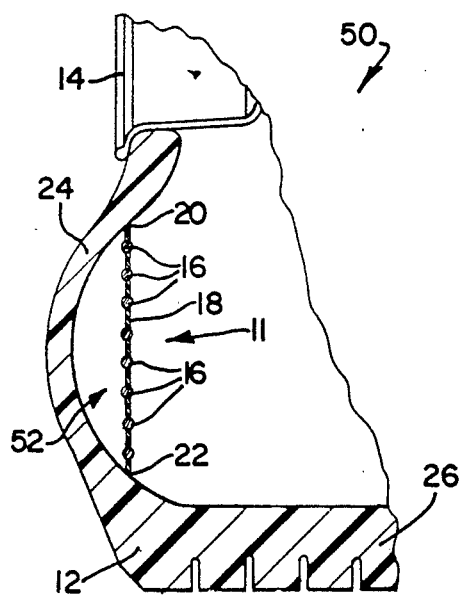

Referring to FIG. 2, a further embodiment of a transducer 50 is shown therein. This transducer 50 is similar to the embodiment 10 shown in FIG. 1 and is similarly referenced. However, with this embodiment the turns 16 of the coil 11 are all in the same plane in a spiral manner and the membrane 18 is annular. One end of the membrane 18 is secured to the side wall portion 24 close to the rim 14 and the other end 22 is secured to the side wall portion close to the tread portion 26 to define a chamber 52. The operation of this system is similar to that of FIG. 1 and is not discussed further.

Figure 3:
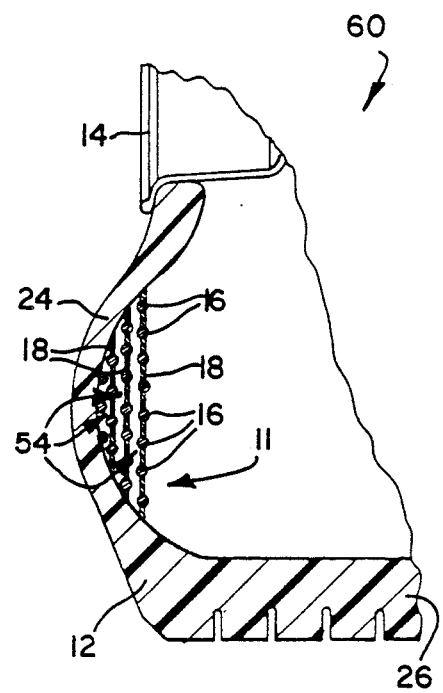

Referring to FIG. 3 a further embodiment of a transducer 60 is shown. This transducer 60 has four layers, with a first layer of turns secured to the side wall portion 24 and successive turns 16 being secured to three membranes 18. A series of chambers 54 are defined and the operation of the system is again similar to the transducers 10 and 50 and will be understood by those skilled in the art without further discussion thereof.

Figure 4:
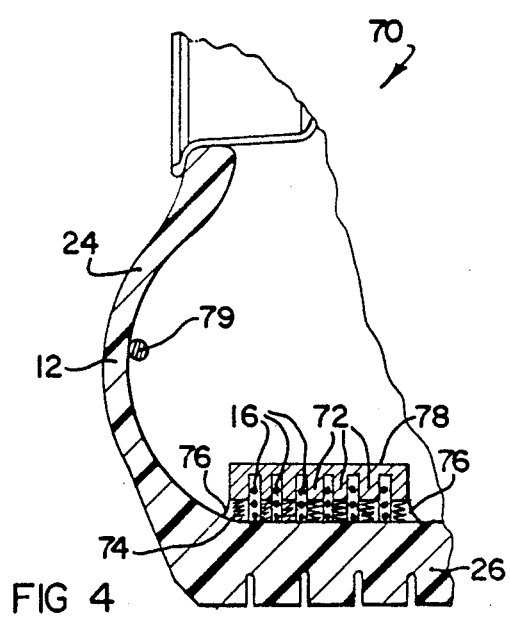

Referring to FIG. 4, a further embodiment of a transducer 70 is shown. With this embodiment different turns 16 of the coil are separated by members 72 which are of a suitable dielectric material having a predetermined permittivity. The members 72 are connected to a cylindrical base portion 78, the ends of which are flexibly connected to the inner surface of the tread portion 26 by membranes 76 to define a chamber. The members 72 are mounted in any suitable resilient manner, for example by spring elements 74 so that the degree to which the members 72 extend between the turns 16 varies in accordance with the pressure within the tire 12. A single turn coil 79 is provided adjacent the side wall portion 24 of the tire 12 to act as a pick-up. The operation of this embodiment 70 is similar to the previous embodiments, it being appreciated that the characteristic inductance and/or capacitance of the coil formed by the turns 16 will vary in accordance with the extent to which the members 72 extend between the turns 16.

Referring to FIG. 5, a further embodiment of a transducer 80 is shown. With this embodiment the turns 16 of the coil 11 are secured to raised formations 82 which project inwardly from the inner surface of the side wall portion 24. With this embodiment, as the pressure in the tire 12 varies, so the degree of flexing of the side wall portion 24 will vary, thereby varying the separation of the turns 16 which accordingly affects the characteristic inductance and/or capacitance to vary the natural frequency of oscillation thereof.

Referring now to FIG. 6, yet a further embodiment of a transducer is shown, and with reference to the previous figures, is similarly referenced. In this embodiment of the invention, the transducer 10 comprises a coil 90, the coil 90 being formed from a spiral circular winding 92 of conductive wire. As illustrated in FIG. 7, the windings 92 are arranged in layers, with adjacent layers, and adjacent turns of the coil 90 within each layer being separated by corresponding turns of a resilient hollow tube 94 of a non-conductive material such as a synthetic plastics material. Each section of tube 94 separates adjacent turns of the conductors 92. The tube 94 and the conductors 12 are encapsulated in a resilient potting compound 96 such as silicone rubber.

Figure 9:
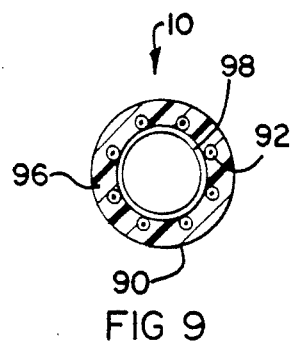
Figure 10:
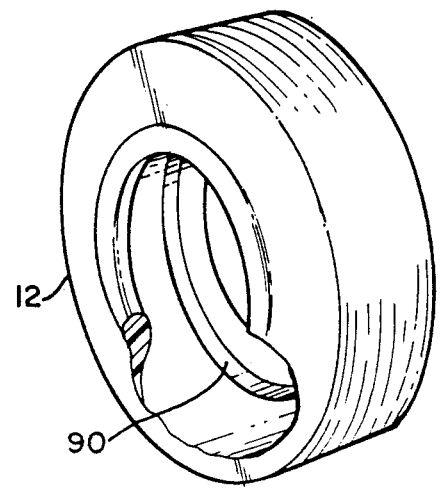
FIG. 10 shows a partly sectioned three dimensional view of a tire including the transducer of FIG. 6.

FIGS. 8 and 9 illustrate various embodiments of the transducer 10. In the embodiment of the invention illustrated in FIG. 8, the conductors 92 are wound in three layers, with the turns of adjacent layers being separated by corresponding turns of the tube 94. Adjacent turns in the same layer are separated only by the resilient potting compound 96.

In FIG. 9, the conductors 12 are arranged about a central resilient tube 98 which is of a non-conducting material, such as a synthetic plastics material. The conductors 92 are held in place about the tube by the potting compound 96.

If the resilient tubes 94 or 98 are sealed, changes in the pressure of air surrounding the transducer 10 will tend to compress them or to allow them to expand. The degree of compression or expansion which occurs is increased by the relative ease with which the tubes 94 or 98 can be compressed.

The pressure which is applied to the transducer 10 will cause the tubes 94 or 98 to be compressed thereby varying the characteristic capacitance or inductance of the coil 90, and in so doing the frequency of oscillation of the coil 90 will vary. The variation of the frequency of oscillation of the coil 90 will be directly proportional to the pressure applied to the coiL 90 by the air within the tire 12.

As an example, a coil having a natural frequency of oscillation of about 1600 kHz may be excited with pulses having a repetition rate of about 160 k-pulses per second in order that suitable damped oscillations are generated in the coil.

Figure 11:
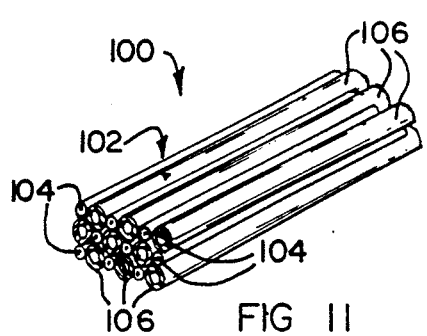
FIG. 11 shows a three dimensional view of a transducer in accordance with the invention for monitoring temperature or humidity of a gas.

Referring now to FIG. 11, a transducer, designated generally by the reference numeral 100 is shown, the transducer 100 being used to monitor the temperature or humidity of a gas.

In this embodiment of the invention, the transducer 100 has a passive monitoring means 102 in the form of a plurality of conductors 104 which are arranged in parallel spaced relationship. A conduit defining means in the form of a length of tube 106, is arranged between adjacent conductors 104. The tubes 106 serve to introduce gas, the temperature or humidity of which is to be monitored, into close proximity to the conductors 104.

In use, as the temperature and/or humidity of the gas within the tubes 106 varies, the permittivity between adjacent conductors 104 will vary, thereby varying the natural frequency of oscillation of the transducer 100.

It will be appreciated, that the transducer 100 will be excited by means of an excitation coil, and the natural frequency of oscillation of the monitoring means 102 will be sensed by a similar sensing coil. Hence, an excitation coil 32 and a sensing coil 34 as described above can be used with the transducer 100, the circuitry for the coils 32 and 34 also being the same as that described above.

We claim:

1. A passive electrically operable monitoring means for use with a transducer for monitoring a physical parameter, the monitoring means having an inherent resistance and a characteristic capacitance and inductance only, the characteristic capacitance and inductance being responsive to variations in the physical parameter such that the monitoring means has a natural frequency of oscillation that varies in accordance with variations in the physical parameter.

2. The monitoring means as claimed in claim 1, which includes a length of conducting wire wound into a coil with spaces being provided between adjacent turns of the coil.

3. The monitoring means as claimed in claim 2 in which the turns are resiliently arranged relative to one another.

4. The monitoring means as claimed in claim 3 in which the physical parameter being monitored is force and which includes a resiliently flexible web arranged between the turns of the coil, with the turns being secured to the web so that, in use, as the web flexes under the effect of the force being monitored, the spacing between the turns varies, thereby varying the characteristic inductance and capacitance of the coil, and hence its natural frequency of oscillation.

5. The monitoring means as claimed in claim 2 which includes a conduit defining means comprising a length of tube which is coiled with the length of wire of the coil so that the tube is arranged between the turns of the coil.

6. The monitoring means as claimed in claim 2 in which the physical parameter being monitored is force and which includes a dielectric medium located between the turns of the coil, the permittivity of the dielectric medium being variable in response to variations in the force applied thereto, for varying the natural frequency of oscillation.

7. The monitoring means as claimed in claim 1 which comprises at least two lengths of spaced conductors arranged in parallel spaced relationship relative to one another.

8. The monitoring means as claimed in claim 7 in which the physical parameter being monitored is force and in which the spacing between the conductors is variable to vary the natural frequency of oscillation of the monitoring means.

9. The monitoring means as claimed in claim 7 in which the physical parameter being monitored is temperature and which includes a conduit defining means for defining a conduit whereby a gas can be introduced into spaces in proximity to the conductors so that as the temperature of the gas varies the permittivity of the gas between the conductors varies thereby varying the natural frequency of oscillation.

10. The monitoring means as claimed in claim 7 in which the physical parameter being monitored is force and which includes a dielectric medium located between the lengths of conductors, the permittivity of the dielectric medium being variable in response to variations in the force applied thereto, for varying the natural frequency of oscillation.

11. A transducer for monitoring a physical parameter, the transducer including
   a monitoring means as claimed in claim 1;
   an energising means for energising the monitoring means; and
   a sensing means for sensing the natural frequency of oscillation of the monitoring means.

12. The transducer as claimed in claim 11 in which the energising means includes an energising coil which is coupled electrically and/or magnetically to the monitoring means in a wireless manner for energising the monitoring means to cause the monitoring means to oscillate at its natural frequency of oscillation.

13. The transducer as claimed in claim 12 which includes a pulse generating means for generating a string of pulses at a repetition rate sufficiently lower than the natural frequency of oscillation of the monitoring means so that damped oscillations occur in the monitoring means, in use.

14. The transducer as claimed in claim 11, in which the sensing means includes a sensing coil which is electrically and/or magnetically coupled to the monitoring means in a wireless manner.

15. A tire which includes
   a casing; and
   a monitoring means as claimed in claim 1 inclusive mounted within and rotatably fast with the casing.

16. A method of monitoring a physical parameter which includes
   energising a passive electrical monitoring means having only a characteristic capacitance and inductance and an inherent resistance so that the monitoring means oscillates at a natural frequency of oscillation;
   causing the characteristic capacitance and the characteristic inductance to vary in response to variations in the parameter being monitored thereby to vary the natural frequency of oscillation of the monitoring means; and
   sensing the variations in the natural frequency of oscillation of the monitoring means to provide an indication of the value of the parameter being monitored.

17. The method as claimed in claim 16, in which the parameter being monitored is force, the monitoring means comprises a length of conducting wire wound into a coil to provide a plurality of spaced turns, and in which the method includes varying the spacing between the coils to vary the characteristic capacitance and inductance of the coil, and hence its natural frequency of oscillation, in response to variations in the force being applied to the coil.

18. The method as claimed in claim 16 in which the monitoring means comprises at least two lengths of spaced conductors which are arranged in parallel spaced relationship relative to one another, and in which, when the parameter being monitored is force, the method includes varying the spacing between the conductors.

19. The method as claimed in claim 16 in which the monitoring means comprises at least two lengths of spaced conductors which are arranged in parallel spaced relationship relative to one another, and in which, when the parameter being monitored is temperature, the method includes introducing a gas into a space in proximity to the conductors so that as the temperature of the gas varies, the permittivity of the gas between the conductors varies thereby varying the natural frequency of oscillation.

20. The method as claimed in claim 16 in which the parameter being monitored is force, and monitoring means comprises a length of conducting wire wound into a coil to provide a plurality of spaced turns, and in which the method includes varying the permittivity of a medium between the turns in response to variation in the said force thereby to vary the natural frequency of oscillation of the coil.

21. The method as claimed in claim 20 which includes locating a suitable material between the turns, the material being allowed to expand or to be compressed as the force being monitored, and which is exerted on the material, varies so that the permittivity of the material varies.

22. The method as claimed in claim 21 which includes introducing a suitable material between the elements in proportion to the force being monitored, sot hat the permittivity of the medium between the turns varies.

23. The method as claimed in claim 16 which includes energising the monitoring means with a string of pulses.

24. The method as claimed in claim 23 which includes energising the monitoring means with a string of pulses which has a repetition rate suitably lower than the natural frequency of oscillation of the monitoring means so that damped oscillations occur in the monitoring means.

25. The method of monitoring as claimed in claim 16 in which the physical parameter being monitored is humidity and which includes a conduit defining means for defining a conduit whereby a gas, the humidity of which is to be monitored, can be introduced into spaces in proximity to the conductors so that as the humidity of the gas varies the permittivity of the gas between the conductors varies thereby varying the natural frequency of oscillation.

26. The method as claimed in claim 16 in which the monitoring means comprises at least two lengths of spaced conductors which are arranged in parallel spaced relationship relative to one another and in which, when the parameter being monitored is humidity, the method includes introducing a gas into a space in proximity to the conductors so that as the humidity of the gas varies, the permittivity of the gas between the conductors varies thereby varying the natural frequency of oscillation.

* * * * *